(12) United States Patent
Borvan

(10) Patent No.: US 11,376,382 B2
(45) Date of Patent: Jul. 5, 2022

(54) ORAL MANDIBULAR AIRWAY DEVICE AND METHOD

(71) Applicant: Daniel W. Borvan, Frankfort, IL (US)

(72) Inventor: Daniel W. Borvan, Frankfort, IL (US)

(*) Notice: Subject to any disclaimer, the term of this patent is extended or adjusted under 35 U.S.C. 154(b) by 204 days.

(21) Appl. No.: 16/224,323

(22) Filed: Dec. 18, 2018

(65) Prior Publication Data
US 2020/0188622 A1    Jun. 18, 2020

(51) Int. Cl.
*A61M 16/04* (2006.01)
*A61M 16/01* (2006.01)
(Continued)

(52) U.S. Cl.
CPC ........ *A61M 16/0495* (2014.02); *A61M 16/01* (2013.01); *A61M 16/0463* (2013.01);
(Continued)

(58) Field of Classification Search
CPC .............. A61M 16/00; A61M 16/0087; A61M 16/009; A61M 16/01; A61M 16/04; A61M 16/0463; A61M 16/0475; A61M 16/0477; A61M 16/0488–0497; A61M 16/22; A61M 2202/00–0014; A61M 2202/02; A61M 2202/0208; A61M 2202/0225;
(Continued)

(56) References Cited

U.S. PATENT DOCUMENTS 3,211,149 A * 10/1965 Fono .................. A61C 17/0211
                                                        604/37
4,560,351 A * 12/1985 Osborne ................ A61C 19/08
                                                        433/215
(Continued)

FOREIGN PATENT DOCUMENTS

CA          2192028 A1    1/1998
CN        106659553 A     5/2017
(Continued)

OTHER PUBLICATIONS

International Search Report dated Feb. 28, 2020 issued in connection with corresponding PCT Application No. PCT/US19/66591.
(Continued)

*Primary Examiner* — Michelle J Lee
(74) *Attorney, Agent, or Firm* — Akerman LLP

(57) ABSTRACT

The present invention provides an oral device that is inserted into the mouth of a patient during sedation to minimize the risk of airway obstruction and method of use. The oral device comprises a mouthpiece. A gas inlet conduit, a gas outlet conduit, and a fluid outlet conduit are adjacent to the vestibular portion of the mouthpiece. The gas inlet conduit may be used to provide oxygen to the mouth of a patient. The gas outlet conduit may be used to remove end-tidal carbon dioxide from the mouth of a patient. The fluid outlet conduit may be used to remove fluid from the mouth of a patient. The oral device may also include a tongue stabilizer to minimize movement of the tongue. The mouthpiece may include fluid outlet ports to remove fluid from the mouth of a patient and an instrument passage to allow medical instruments to pass through the oral device.

19 Claims, 10 Drawing Sheets

(51) Int. Cl.
*A61M 16/22* (2006.01)
*A61C 17/02* (2006.01)

(52) U.S. Cl.
CPC ..... *A61M 16/22* (2013.01); *A61M 2202/0208* (2013.01); *A61M 2210/0625* (2013.01)

(58) Field of Classification Search
CPC ... A61M 2202/0241; A61M 2210/0625–0643; A61M 16/042; A61M 2202/0466; A61C 19/06; A61C 19/063; A61C 19/08; A61C 17/00; A61C 17/02; A61C 17/0208–028; A61C 17/10–135; A61F 5/56–566
See application file for complete search history.

(56) References Cited

U.S. PATENT DOCUMENTS

| | | | | |
|---|---|---|---|---|
| 5,104,315 | A * | 4/1992 | McKinley | A61C 17/024 433/80 |
| 8,122,889 | B2 * | 2/2012 | Vaska | A61F 5/566 128/207.14 |
| 9,308,064 | B2 * | 4/2016 | Binner | A61C 17/0205 |
| 2005/0037315 | A1 | 2/2005 | Inoue et al. | |
| 2005/0197529 | A1 | 9/2005 | Hoshihara et al. | |
| 2009/0241969 | A1 | 10/2009 | Walker | |
| 2010/0242969 | A1 | 9/2010 | Lyons | |
| 2011/0027746 | A1 * | 2/2011 | Mcdonough | A61C 17/0202 433/80 |
| 2011/0318705 | A1 * | 12/2011 | Sullivan | A61C 17/0211 433/80 |
| 2013/0068235 | A1 * | 3/2013 | Makower | A63B 71/085 128/860 |
| 2016/0067081 | A1 * | 3/2016 | Sorresso | A61M 16/0493 128/847 |
| 2016/0106571 | A1 * | 4/2016 | Vaska | A61M 16/0488 128/847 |
| 2016/0361192 | A1 | 12/2016 | Gerschman et al. | |
| 2017/0151400 | A1 | 6/2017 | Vaska et al. | |
| 2018/0000573 | A1 | 1/2018 | Miller et al. | |
| 2018/0036108 | A1 | 2/2018 | Cardinale et al. | |

FOREIGN PATENT DOCUMENTS

| | | |
|---|---|---|
| EP | 0818213 A2 | 1/1998 |
| WO | 2014/144717 A2 | 9/2014 |

OTHER PUBLICATIONS

Written Opinion dated Feb. 28, 2020 issued in connection with corresponding PCT Application No. PCT/US19/66591.
Office Action dated Jul. 12, 2021 issued in connection with corresponding Canadian Patent Application No. 3,121,590.
Search Report dated Jan. 7, 2022 issued in connection with European Patent Application No. 19899689.4.
Examination Report dated Jan. 10, 2022 issued in connection with UK Patent Application No. 2108096.5.
Notification of the First Office Action and Search Report dated Jan. 26, 2022 issued in connection with Chinese Patent Application No. 2019800838096.

* cited by examiner

_US 11,376,382 B2_

ORAL MANDIBULAR AIRWAY DEVICE AND METHOD

BACKGROUND OF THE INVENTION

The present invention relates to an oral mandibular airway device and method. Medical patients may be given anesthesia as part of a medical procedure. There is generally four main types of anesthesia, namely local, regional, monitored (IV), and general. Local anesthesia involves an injection of medication that numbers a small area of the body. Regional anesthesia is typically administered through an injection or catheter and is used to numb a section of the body. Monitored anesthesia, also known as IV sedation, is administered through a vein. Depending on the level of anesthesia used, patients may be able to talk or be in a deep sleep. General anesthesia is administered either through a mask on the face or intravenous until the patient loses consciousness.

As the level of sedation for a patient is increased, it may be necessary to control the breathing of a patient. In a deep sleep or general sedation state, certain invasive devices may be used by a medical professional to control breathing. For example, the oral pharyngeal airway and the nasal pharyngeal airway are used during general anesthesia and they can also be inserted under deep sedation. Airway devices such as the laryngeal mask, the endotracheal tube, the gastro laryngeal tube and the gastro mask may be used to control breathing and maintain an open airway of a patient during deep sleep or general sedation. However, these devices generally require a patient to be in a deep sleep or general sedation state for the patient to tolerate the invasiveness into the airway. For sedation states less than deep sleep or general sedation, the invasiveness of the devices may cause undesirable side effects of patient retching or vomiting.

Thus, it may be advantageous to provide a device that a medical professional can use during monitored anesthesia to control breathing and maintain an open airway of a patient without causing undesirable side effects.

SUMMARY OF THE INVENTION

The present invention is directed to an oral device comprising a mouthpiece for insertion into a mouth, said mouthpiece having a vestibular portion, an oral cavity portion, an upper portion and a lower portion, wherein said upper portion is configured to hold upper teeth of said mouth and said lower portion is configured to hold lower teeth of said mouth. The device includes a first gas conduit adjacent to said vestibular portion of said mouthpiece, wherein said first gas conduit has a first opening outside said mouth and a second opening inside said mouth and is configured to allow gas to flow between said first opening and said second opening. The device includes a second gas conduit adjacent to said vestibular portion of said mouthpiece, wherein said second gas conduit has a first opening outside said mouth and a second opening inside said mouth and is configured to allow gas to flow between said second opening and said first opening. The device includes a first fluid conduit adjacent to said vestibular portion of said mouthpiece, wherein said first fluid conduit has a first opening outside said mouth and a second opening inside said mouth and is configured to allow gas to flow between said second opening and said first opening.

Another embodiment of the present invention is directed to an oral device for a patient comprising a mouthpiece for insertion into a mouth, said mouthpiece having a vestibular portion, an oral cavity portion, an upper portion and a lower portion, wherein said upper portion is configured to hold upper teeth of said mouth and said lower portion is configured to hold lower teeth of said mouth. The oral device includes an oxygen conduit attached to said upper portion of said mouthpiece for providing oxygen to inside the mouth of a patient from outside the mouth of said patient. The oral device includes an end-tidal carbon dioxide conduit attached to said upper portion of said mouthpiece for providing end-tidal carbon dioxide from inside the mouth of said patient to outside the mouth of said patient. The oral device includes a saliva conduit attached to said lower portion of said mouthpiece for removing saliva from inside the mouth of said patient to outside the mouth of said patient.

Another embodiment of the present invention is directed to a method of minimizing airway obstruction during sedation. The method comprises inserting an oral device into the mouth of a patient, wherein said device includes a mouthpiece, an oxygen conduit, an end-tidal carbon dioxide conduit, a saliva conduit, and a tongue stabilizer. The method includes immobilizing the jaw of said patient by engaging said mouthpiece with the teeth of said patient. The method also includes immobilizing the tongue of said patient by engaging said tongue stabilizer with the tongue of said patient. The method also includes providing oxygen to said mouth of said patient through said oxygen conduit and removing end-tidal carbon dioxide from said mouth of said patient through said end-tidal conduit.

DETAILED DESCRIPTION OF THE INVENTION

Figure 1A:
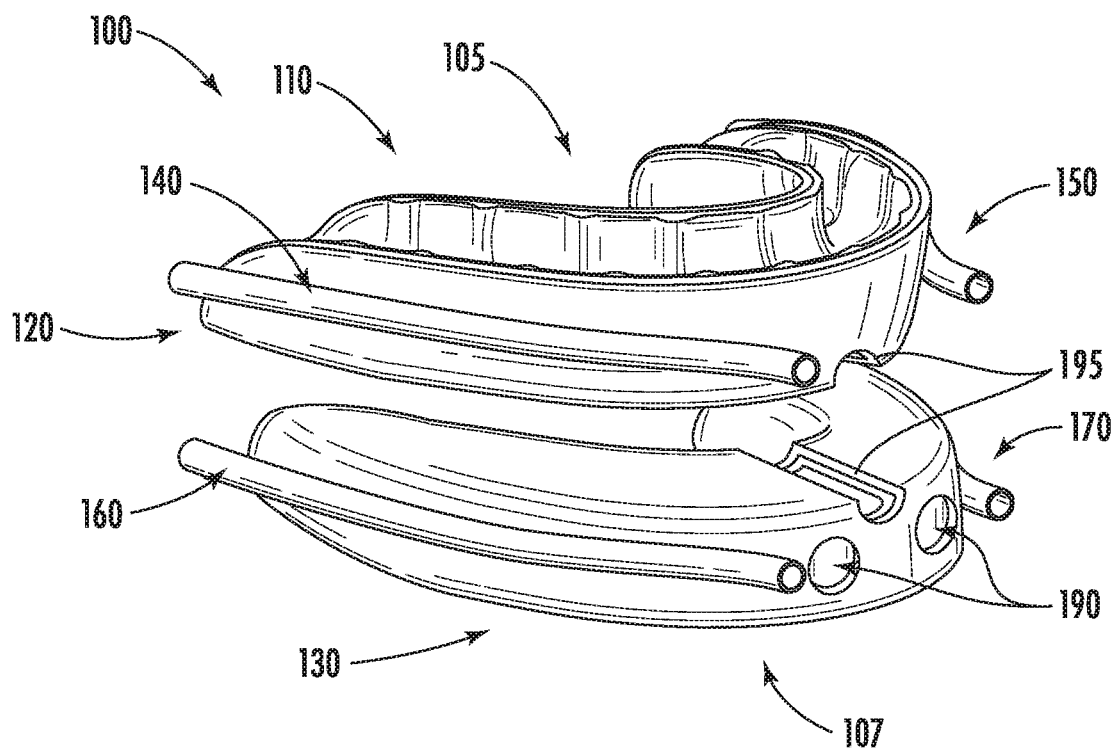
FIG. 1A is a perspective view of an embodiment of the oral device.
Figure 1B:
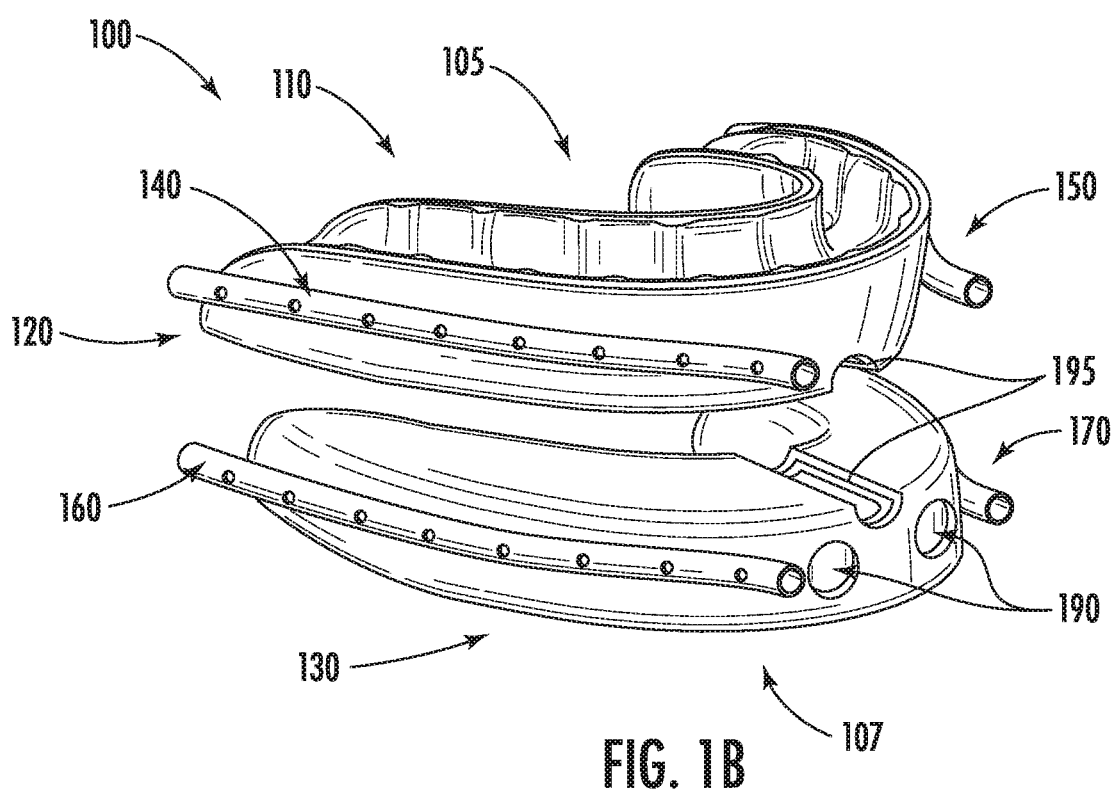
FIG. 1B is a perspective view of an embodiment of the oral device.

As shown in FIGS. 1A and 1B, an oral device 100 consists of a mouthpiece 110, a gas inlet conduit 140, a gas outlet conduit 150, and a fluid outlet conduit 160. The oral device 100 may also include a second fluid outlet conduit 170, at least one fluid outlet port 190, and a medical instrument passage 195. The oral device 100 may be inserted into the mouth of a patient during sedation. The oral device 100 is non-invasive and may be tolerated by a patient under moderate to deep sedation and minimizing the risk of causing coughing, retching, or vomiting.

FIG. 1A illustrates an embodiment of the invention where the gas inlet conduit 140, gas outlet conduit 150, fluid outlet conduit 160 and second fluid outlet conduit 170 are tubes with openings at each end. FIG. 1B illustrates an embodiment of the invention where the gas inlet conduit 140, gas outlet conduit 150, fluid outlet conduit 160 and second fluid outlet conduit 170 are tubes with openings at each end, but also include openings on the sides of the tubes in the portion of the tubes that reside in the mouth of a patient during operation. For example, for the gas inlet conduit 140, gas would be supplied to the mouth of a patient through the opening at the end of the gas inlet conduit 140 and the holes on the sides of the gas inlet conduit 140. For the gas outlet conduit 150, gas would be extracted from the mouth of the patient through the end of the gas outlet conduit 150 and the holes on the sides of the gas outlet conduit 150. For the fluid outlet conduit 160 and the second fluid outlet conduit 170, fluid would be extracted from the mouth of the patient through the end of the fluid outlet conduit 160 and second fluid outlet conduit 170 and the holes on the sides of the fluid outlet conduit 160 and holes on the second fluid outlet conduit 170. Any combination of conduits 140, 150, 160, and 170 with holes on the sides of the conduits or without holes on the sides of the conduits may be used. In addition, any number of holes may be used on the conduits 140, 150, 160, and 170.

Figure 1C:
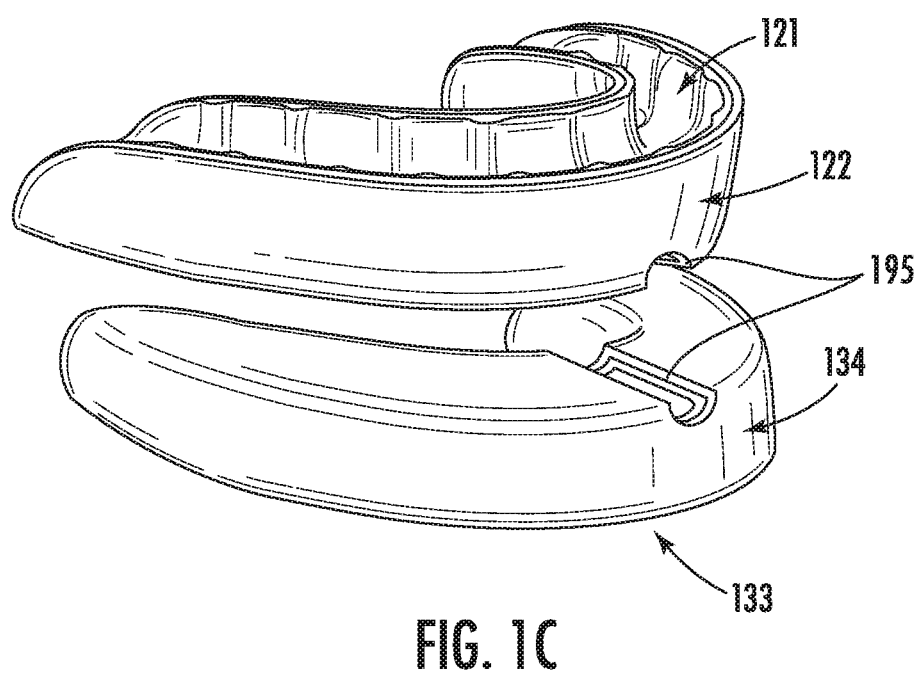
FIG. 1C is a perspective view of the mouthpiece.

Mouthpiece 110 includes an upper portion 120 and a lower portion 130. Mouthpiece 110 is generally a "U" shape for insertion into a patient's mouth, but may be other shapes. The posterior of the "U" shaped mouthpiece 110 includes an oral cavity portion of the mouthpiece 105. The oral cavity portion of the mouthpiece 105 may include an open space, may include a connecting piece between the posterior "U" shaped portions, or may be a solid piece. The anterior of the "U" shaped mouthpiece 110 includes a vestibular portion 107 that faces the interior of the cheek and lips of a patient. As discussed herein, the vestibular portion 107 of the mouthpiece refers to the outer portion of the mouthpiece that faces the cheek and lips of a patient. As shown in FIG. 1C, the upper portion 120 of the mouthpiece 110 has a top 121 and a bottom 122. The lower portion 130 of the mouthpiece 110 has a bottom 133 and a top 134.

As shown in FIGS. 1A, 1B, and 1C, the oral device may include an instrument passage 195. The instrument passage 195 may be an opening in the mouthpiece 110 to allow a medical instrument to pass through the mouthpiece 110, for example a camera or scope that a medical professional may desire to insert into or through the mouth of a patient. For example, in certain medical procedures it may be desirable to insert a scope or camera through the mouthpiece 110, through the mouth, and into the stomach of a patient. The instrument passage 195 may be an opening in the bottom of upper portion 122 of the mouthpiece 110. The instrument passage 195 may be an opening in the top of the lower portion 134 of the mouthpiece 110. Alternatively the instrument passage 195 may only be an opening on the bottom of the upper portion 122 of the mouthpiece 110 or the top of the lower portion 134 of the mouthpiece 110. Any opening to allow a medical instrument to pass through the mouthpiece 110 is contemplated as part of the invention.

Figure 2:
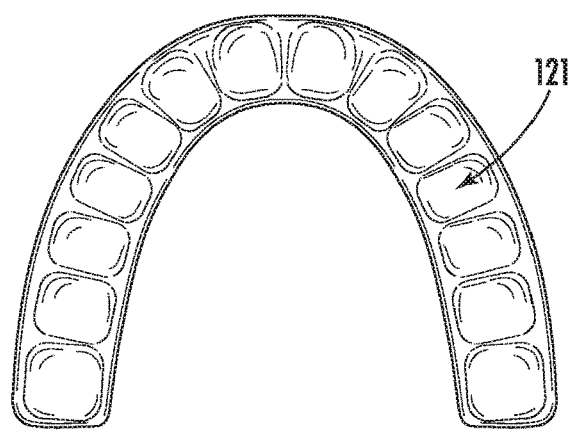
FIG. 2 is a top view of the upper portion of the mouthpiece.
Figure 3:
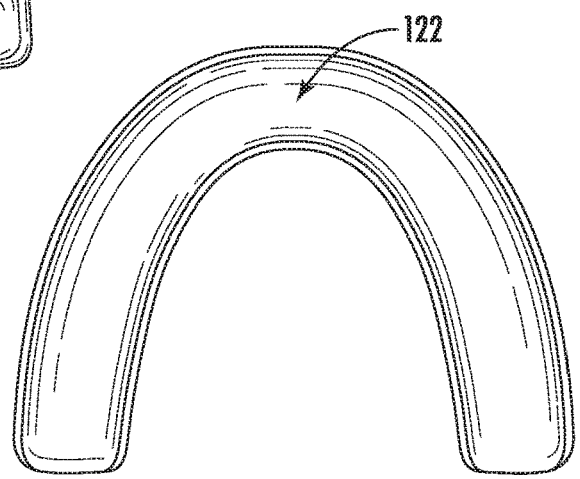
FIG. 3 is a bottom view of the upper portion of the mouthpiece.
Figure 4:
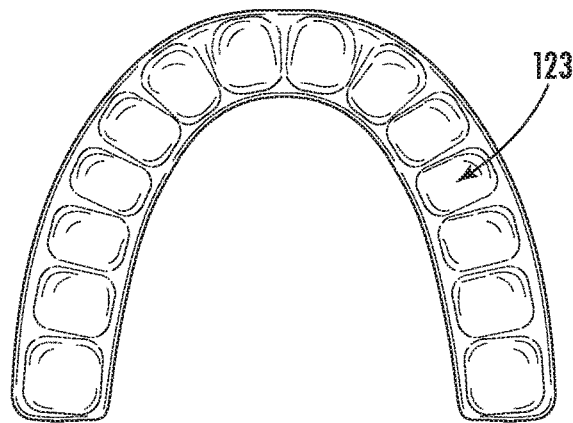
FIG. 4 is a bottom view of the lower portion of the mouthpiece.
Figure 5:
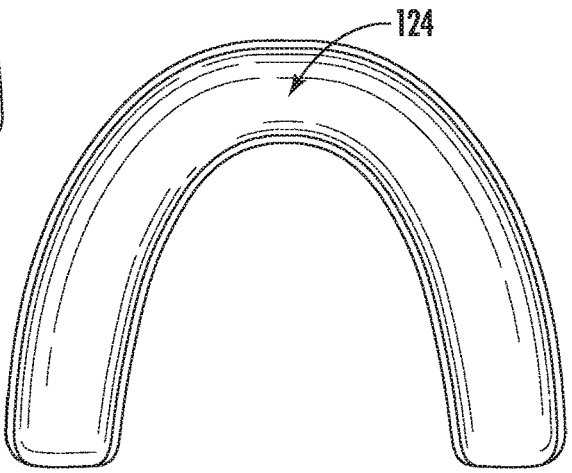
FIG. 5 is a top view of the lower portion of the mouthpiece.

FIG. 2 shows the top of upper portion 121 of the mouthpiece 110. FIG. 3 shows the bottom of upper portion 122 of the mouthpiece 110. FIG. 4 shows the bottom of the lower portion 133 of the mouthpiece 110. FIG. 5 shows the top of the lower portion 134 of the mouthpiece 110. Preferably mouthpiece 110 may be made of a plastic material, but it is contemplated that mouthpiece 110 may be made of other materials. A patient's teeth may engage the top of upper portion 121 and the bottom of lower portion 133. In an embodiment, the comfort of the patient may be enhanced by making the top of the upper portion 121 and the bottom of the lower portion 133 from a relatively soft material such that the patient's teeth can comfortably engage the mouthpiece 110. In an embodiment, the bottom of the upper portion 122 and the top of the lower portion 134 are made of a harder plastic material than the top of the upper portion 121 and the bottom of the lower portion 133. The gas inlet conduit 140, gas outlet conduit 150, fluid outlet conduit 160 and the second fluid outlet conduit 170 may be made of a plastic material and attached to the vestibular portion 107 of mouthpiece 110.

Figure 6:
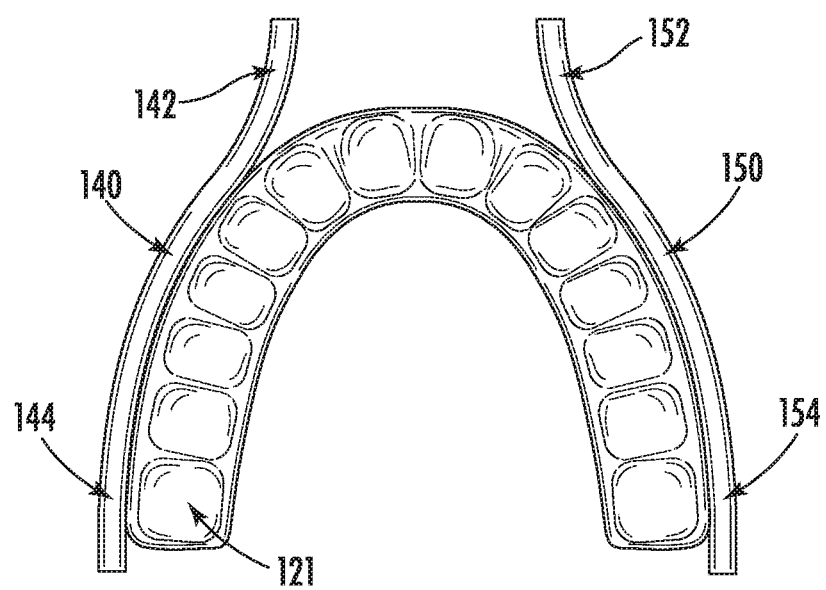
FIG. 6 is a top view of the upper portion of the oral device.
Figure 7:
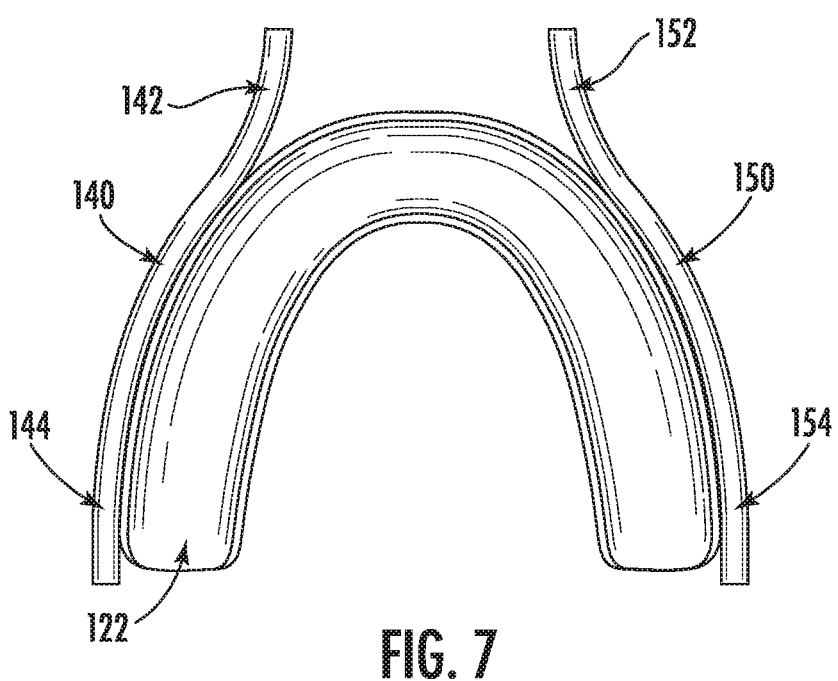
FIG. 7 is a bottom view of the upper portion of the oral device.

FIGS. 6, 7, 8 and 9 illustrate an embodiment of the present invention. FIG. 6 shows a top of upper portion 121, gas inlet conduit 140, and gas outlet conduit 150. FIG. 7 shows the bottom of upper portion 122, gas inlet conduit 140, and gas outlet conduit 150. In an embodiment, gas inlet conduit 140 and gas outlet conduit 150 are tube shaped with an interior lumen for transmitting gas to and from a patient's mouth. The gas inlet conduit 140 and gas outlet conduit 150 may be attached to the vestibular portion 107 of the upper portion 120 of mouthpiece 110. Alternatively, the gas inlet conduit 140 and gas outlet conduit 150 may be attached to the vestibular portion 107 of the lower portion 130 of mouthpiece 110.

Gas inlet conduit 140 has an exterior opening 142 that is outside the mouth of a patient and an interior opening 144 that is inside the mouth of a patient during operation. A gas, such as oxygen, may be provided at the exterior opening 142, transmitted through the gas inlet conduit 140, and communicated into the mouth of a patient at interior opening 144. In an embodiment, an oxygen source may be attached to exterior opening 142. The opening 144 may be of several forms such that the opening is not blocked by the anatomy of the mouth. For example, the opening 144 may be comprised of one or several openings inside the mouth to allow for passage of gas through opening 144 if an opening becomes blocked. An example is illustrated in FIG. 1B.

Gas outlet conduit 150 has an exterior opening 152 that is outside the mouth of a patient and an interior opening 154 that is inside the mouth of a patient during operation. Gas may pass from the interior opening 154 inside the mouth of a patient through gas outlet conduit 150 to the exterior opening 152. In an embodiment, the gas that is communicated through gas outlet conduit is end tidal carbon dioxide. In an embodiment, a person of ordinary skill in the art may connect a monitor to exterior opening 152 to monitor the level of end tidal carbon dioxide exhausted by a patient. The opening 154 may be of several forms such that the opening is not blocked by the anatomy of the mouth. For example, the opening 154 may be comprised of one or several openings inside the mouth to allow for passage of gas through opening 154 if an opening becomes blocked. An example is illustrated in FIG. 1B.

Figure 8:
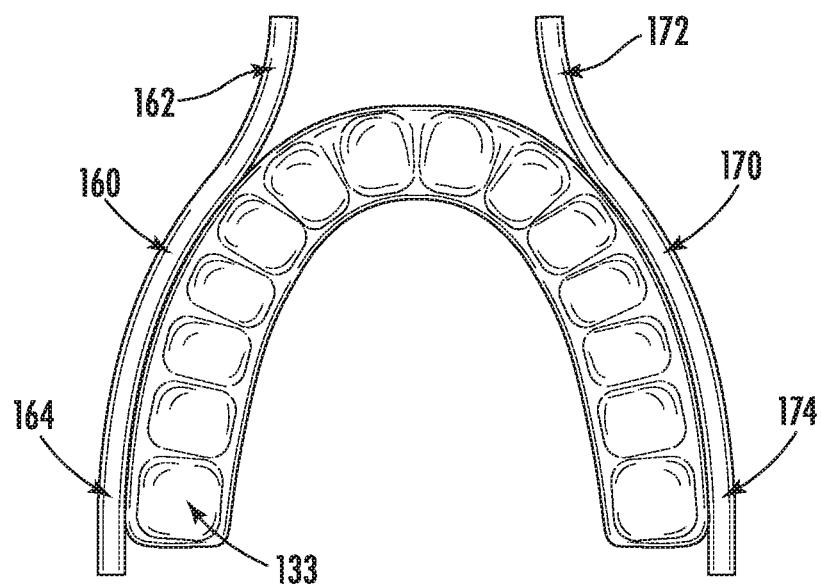
FIG. 8 is a bottom view of the lower portion of the oral device.
Figure 9:
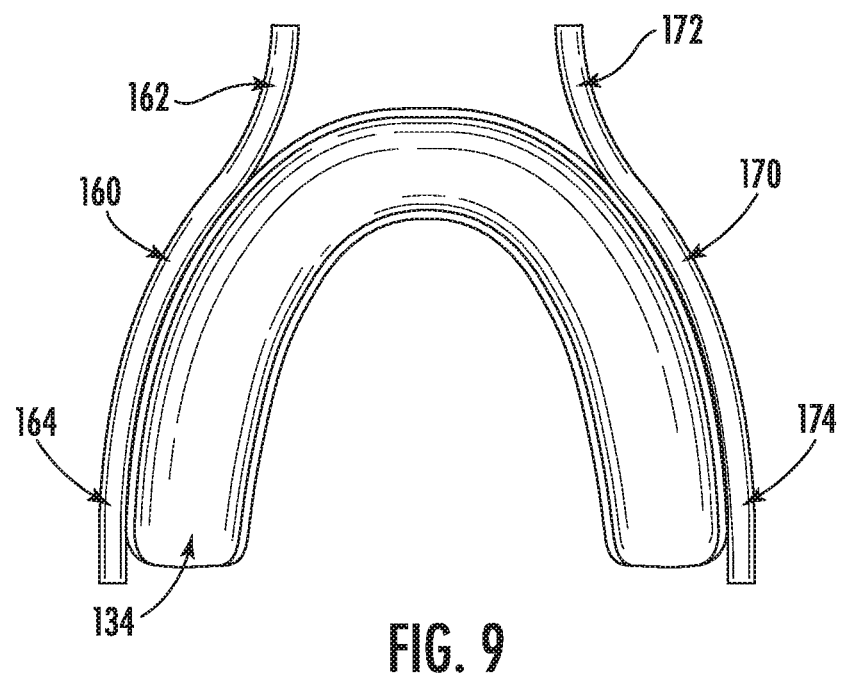
FIG. 9 is a top view of the lower portion of the oral device.

FIG. 7 shows a bottom lower portion 123, fluid outlet conduit 160 and a second fluid outlet conduit 170. FIG. 8 shows a top lower portion, the fluid outlet conduit 160 and the second fluid outlet conduit 170. In an embodiment, fluid outlet conduit 160 and second fluid outlet conduit 170 are tube shaped with an interior lumen for transmitting fluid, such as saliva, from inside the mouth of a patient to outside the mouth of a patient. The fluid outlet conduit 160 and second fluid outlet conduit 170 may be attached to the vestibular portion 107 of the lower portion 130 of mouthpiece 110. Alternatively, fluid outlet conduit 160 and second fluid outlet conduit 170 may be attached to the vestibular portion 107 of the upper portion 120 of mouthpiece 110.

Fluid outlet conduit 160 has an exterior opening 162 that is outside the mouth of a patient and an interior opening 164 that is inside the mouth of a patient during operation. A fluid secretion, such as saliva, may be extracted from the mouth of a patient through the interior opening 164, through the fluid outlet conduit 160, and exhausted through the exterior opening 162 that is outside the mouth. A suction device may be attached to exterior opening 162 to pull saliva through interior opening 164. The interior opening 162 may be of several forms such that the opening is not blocked by the anatomy of the mouth. For example, the opening 162 may be comprised of one or several openings inside the mouth to allow for passage of fluid through opening 162 if an opening becomes blocked. An example is illustrated in FIG. 1B.

In an embodiment, the oral device 100 includes one fluid outlet conduit, for example fluid outlet conduit 160, to remove saliva from the mouth of a patient. Alternatively, as shown in FIGS. 6 and 7, the oral device 100 includes a second fluid outlet conduit 170. The second fluid outlet conduit may be positioned on the oral device 100 to reach a different section of the mouth of a patient than the fluid outlet conduit 160. In an embodiment and as shown in FIGS. 7 and 8, the fluid outlet conduit 160 may be used to reach the left side of a the mouth of a patient and the second fluid outlet conduit 170 may be used to reach the right side of the mouth of a patient.

The second fluid outlet conduit 170 has an exterior opening 172 that is outside the mouth of a patient and an interior opening 174 that is inside the mouth of a patient during operation. A fluid secretion, such as saliva, may be extracted from the mouth of a patient through the interior opening 174, through the second fluid outlet conduit 170, and exhausted through the exterior opening 172 that is outside the mouth. A suction device may be attached to exterior opening 172 to pull saliva through interior opening 174. The interior opening 172 may be of several forms such that the opening is not blocked by the anatomy of the mouth. For example, the opening 172 may be comprised of one or several openings inside the mouth to allow for passage of fluid through opening 172 if an opening becomes blocked. An example is illustrated in FIG. 1B.

Figure 10:
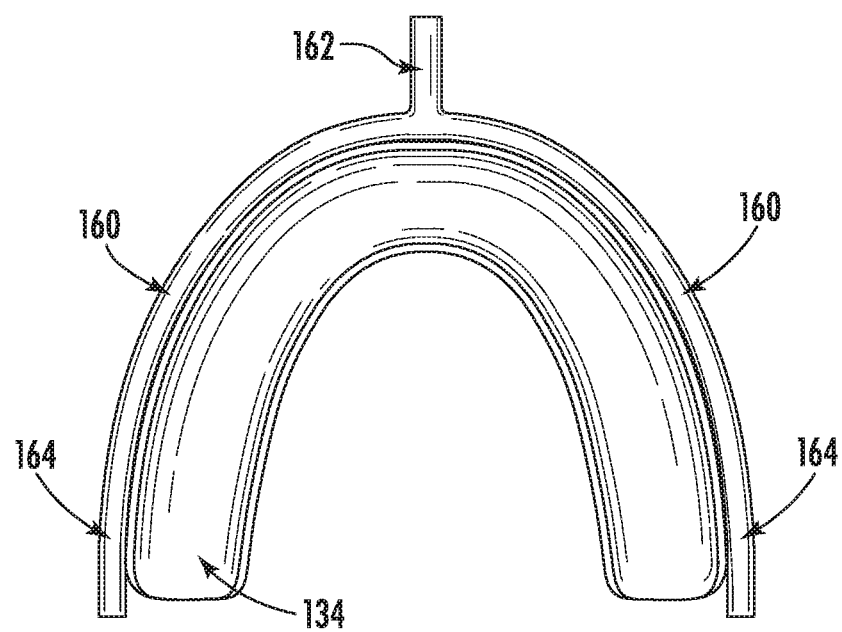
FIG. 10 is a top view of the lower portion of an alternative embodiment of the oral device.
Figure 11:
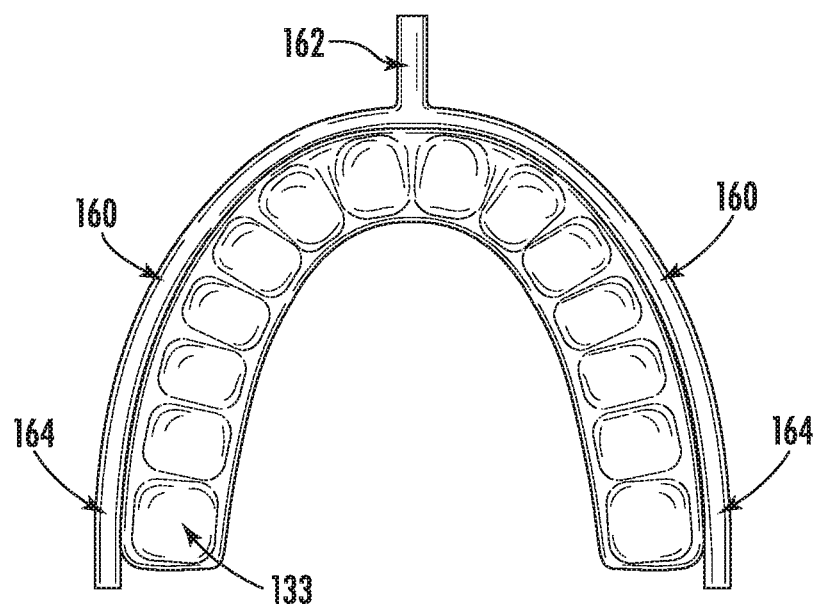
FIG. 11 is a bottom view of the lower portion of an alternative embodiment of the oral device.

FIGS. 10 and 11 illustrates an embodiment of the present invention whereas the fluid outlet conduit 160 has multiple interior openings 164 and a single exterior opening 162. As shown in FIGS. 10 and 11, the fluid outlet conduit 160 extends around the vestibular portion 107 of the lower portion 130 of mouthpiece 110. In the embodiment of FIGS. 10 and 11, the fluid outlet conduit 160 has two interior openings 164 that are inside the mouth of a patient and one external opening 162 that is outside the mouth of a patient. A fluid secretion, such as saliva, may be extracted from the mouth of a patient through the interior openings 164, through the second fluid outlet conduit 160, and exhausted through the exterior opening 162 that is outside the mouth. A suction device may be attached to exterior opening 162 to pull saliva through interior opening 164. The interior openings 162 may be of several forms such that the opening is not blocked by the anatomy of the mouth. For example, the openings 162 may be comprised of one or several openings inside the mouth to allow for passage of fluid through opening 162 if an opening becomes blocked. In the embodiment of FIGS. 10 and 11, the two interior openings 162 are shown, however, any number of interior openings 162 may be used to reach portions of the mouth of a patient.

Figure 12:
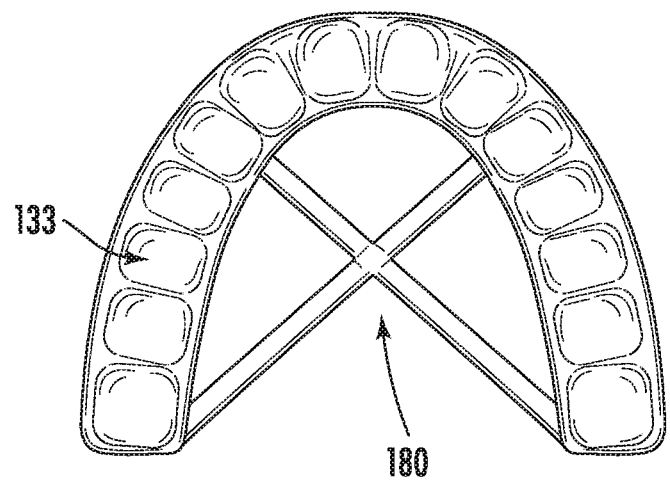
FIG. 12 is a bottom view of the lower portion of an alternative embodiment of the mouthpiece illustrating a tongue stabilizer.

FIG. 12 illustrates an embodiment of the present invention that further includes a tongue stabilizer 180. As shown in FIG. 12, tongue stabilizer 180 is connected to the lower portion of mouthpiece 130 and within the oral cavity portion of the mouthpiece 105. In an alternative embodiment, the tongue stabilizer 180 may be connected to the upper portion of mouthpiece 120 or both the lower portion of mouthpiece 130 and upper portion of mouthpiece 120. As shown in FIG. 12, the tongue stabilizer 180 is composed of two crossbars that intersect in an "X" fashion within the oral cavity 105. During sedation the tongue becomes lax and there is a risk that the tongue may obstruct the airway of a patient. The tongue stabilizer 180 engages the top portion of tongue and holds the tongue in place during sedation. As such, the risk of the tongue obstructing the airway of a patient is reduced.

Figure 13:
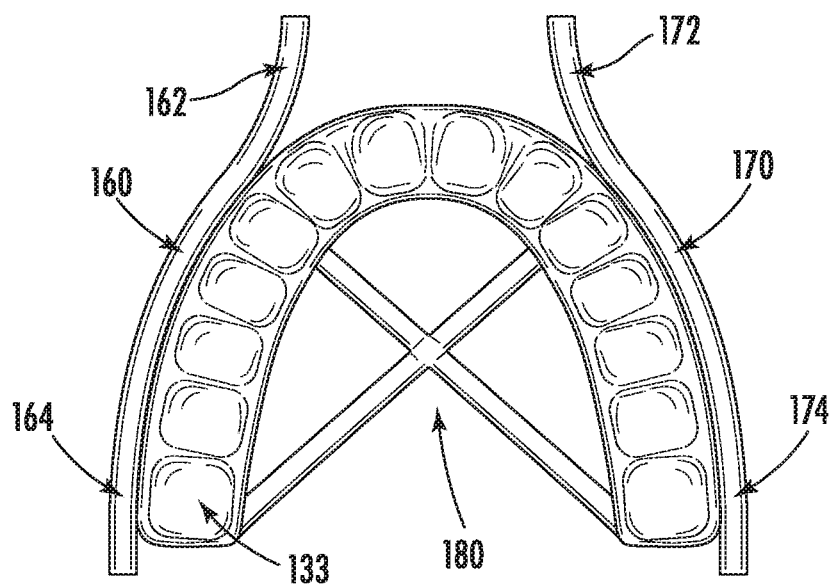
FIG. 13 is a bottom view of the lower portion of an alternative embodiment of the oral device.
Figure 14:
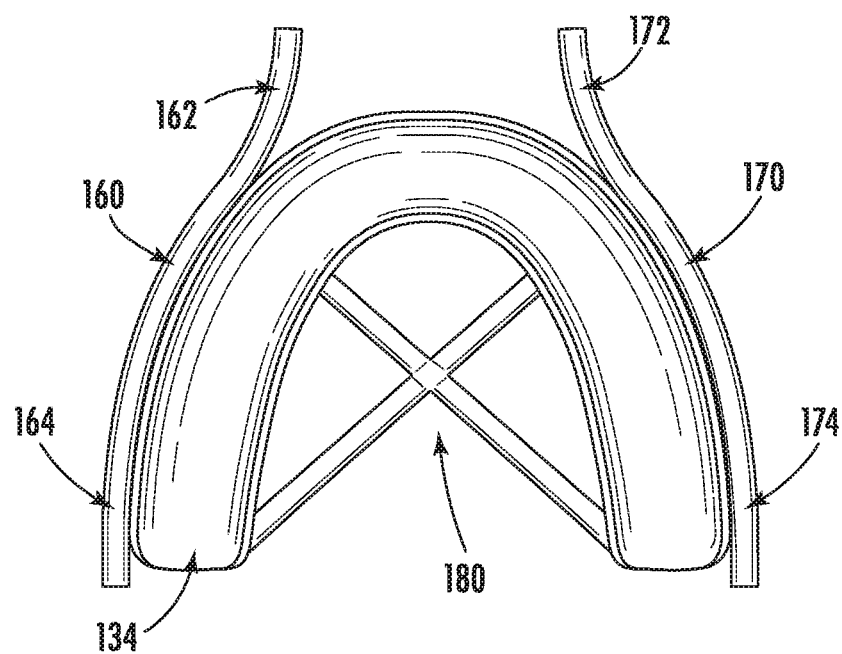
FIG. 14 is a top view of the lower portion of an alternative embodiment of the oral device.

FIG. 13 illustrates the tongue stabilizer 180 connected to the lower portion of mouthpiece 130 from the view point of the bottom of lower portion of the mouthpiece 133. The fluid outlet conduit 160 is shown and the second fluid outlet conduit 170 is shown. FIG. 14 illustrates the tongue stabilizer 180 connected to the lower portion of mouthpiece 130 from the view point of the top of the lower portion of the mouthpiece 134. The fluid outlet conduit 160 is shown and the second fluid outlet conduit 170 is shown. The tongue stabilizer 180 generally contacts the top of the tongue and minimizes movement of the tongue in the mouth. The use of the tongue stabilizer 180 may improve the ability of the fluid outlet conduit 160 and second fluid outlet conduit 170 to remove secretions such as saliva from the mouth because the risk of the tongue blocking the interior openings 164 and 174 is minimized.

Figure 15:
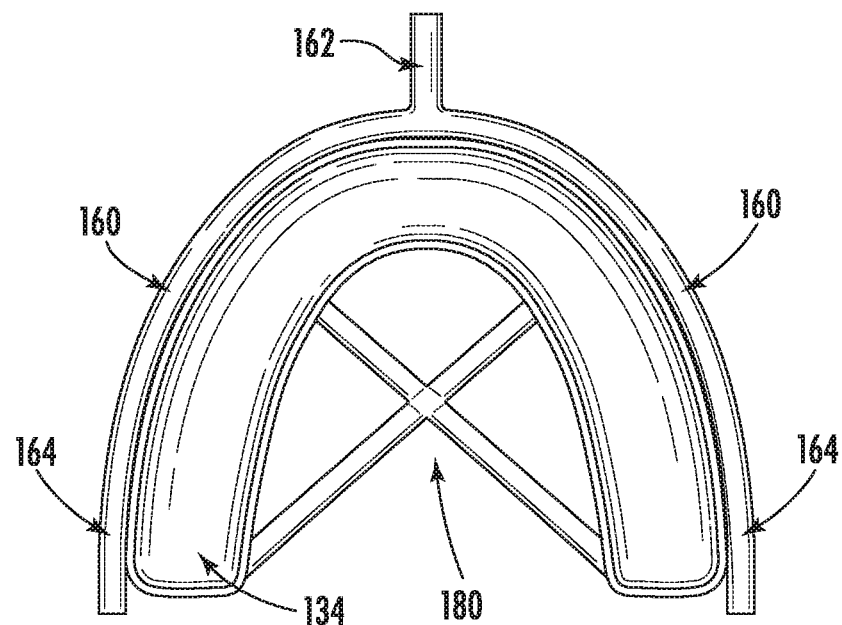
FIG. 15 is a top view of the lower portion of an alternative embodiment of the oral device.
Figure 16:
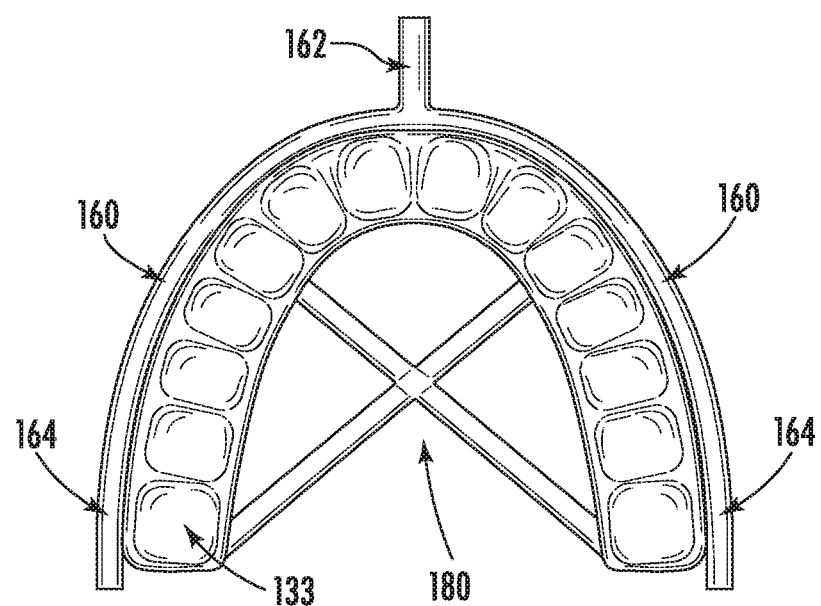
FIG. 16 is a bottom view of the lower portion of an alternative embodiment of the oral device.

FIG. 15 illustrates the tongue stabilizer 180 connected to the lower portion of mouthpiece 130 from the view point of the top of lower portion of the mouthpiece 134. FIG. 16 illustrates the tongue stabilizer 180 connected to the lower portion of mouthpiece 130 from the view point of the bottom of the lower portion of the mouthpiece 133. In both FIGS. 15 and 16, the fluid outlet conduit 160 is shown with two internal openings 164 and a single external opening 162. In this embodiment, the tongue stabilizer 180 generally contacts the top of the tongue and minimizes movement of the tongue in the mouth. The use of the tongue stabilizer 180 may improve the ability of the fluid outlet conduit 160 to remove secretions such as saliva from the mouth because the risk of the tongue blocking the interior openings 164 is minimized.

Figure 17:
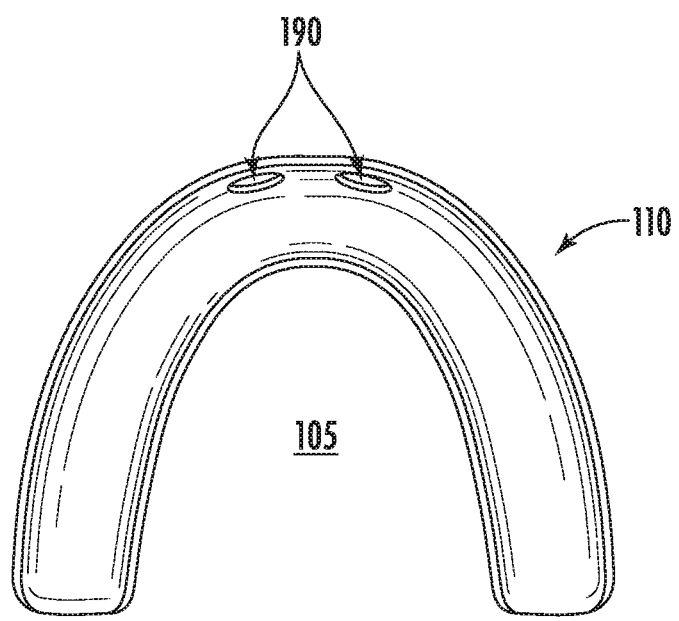
FIG. 17 is a view of the lower portion of the mouthpiece illustrating fluid outlet ports.

FIG. 17 illustrates an embodiment of the present invention that includes at least one fluid outlet port 190 in mouthpiece 110. The fluid outlet port 190 may be one or more holes in the mouthpiece located in the anterior portion of the mouthpiece 110. The fluid outlet port 190 allows access to the oral cavity 105 while the mouthpiece 110 is in the mouth of a patient to remove secretions such as saliva from the oral cavity 105. A suction device may be connected to the exterior of the fluid outlet port 190 to remove saliva from the oral cavity 105. The mouthpiece 110 may include a plurality of fluid outlet ports 190 and the fluid outlet ports 190 may be in the upper portion of the mouthpiece 120 or the lower portion of the mouthpiece 130.

One of ordinary skill in the art would understand that the gas inlet conduit 140 and gas outlet conduit 150 described here may be used with various embodiments of the fluid outlet conduit 160, including the use of a second fluid outlet conduit 170, and the use of one exterior opening of the fluid outlet conduit 162 and multiple interior openings of the fluid outlet conduit 164. In addition, one of ordinary skill in the art would understand the tongue stabilizer 180 may be used with various embodiments of the gas inlet conduit 140, gas outlet conduit 150, fluid outlet conduit 160, and second fluid outlet conduit 170. One of ordinary skill in the art would also understand one or more fluid outlet ports 190 may be used with various embodiments of the invention. These additional oral device designs are contemplated and are included within this description.

In operation, a medical professional may insert the oral device 100 into the mouth of a patient during sedation. The bottom lower portion of the mouthpiece 133 engages the lower teeth of a patient. The top upper portion of the mouthpiece 121 engages the upper teeth of a patient. The engagement of the teeth of a patient supports the jaw as well as the muscles of the mouth, tongue, face and neck which may become lax and lack tone during sedation. The tongue may also be supported and held stationary by the tongue stabilizer 180. The support to the jaw, muscles of the mouth, tongue face and neck may minimize the risk of the airway of a patient becoming blocked during sedation. Additionally, the oral device 100 generally does not extend into the oral pharynx of a patient, which minimizes the risk of stimulating coughing, retching, or vomiting. A source of oxygen may be attached to the exterior opening of the gas inlet conduit 152, communicated through gas inlet conduit 150, and into the mouth of the patient by the interior opening of gas inlet conduit 164. End tidal carbon dioxide may be removed from the mouth of a patient by gas outlet conduit 160. A suction device, measurement device, or other equipment may be attached to the exterior opening of gas outlet conduit 152. End tidal carbon dioxide may pass from the mouth of a patient, into the interior opening in gas outlet conduit 154, through gas outlet conduit 150, and out of the exterior opening in gas outlet conduit 152.

In an embodiment, the lower portion of the mouthpiece 130 is attached to a fluid outlet conduit 160. The fluid outlet conduit 160 may have a one exterior opening 162 and one interior opening 164. In an embodiment, the fluid outlet conduit 160 may have one exterior opening 162 and multiple interior openings 164. In an embodiment, the lower portion of the mouthpiece 130 is also attached to a second fluid outlet conduit 170. A medical professional may remove secretions from the mouth of a patient, such as saliva, through fluid outlet conduit 160 and the second fluid outlet conduit 170. In an embodiment, the mouthpiece may include one or more fluid outlet ports 190. A medical professional may remove secretions from the mouth of a patient, such as saliva, through fluid outlet ports 190. A tongue stabilizer 180 may be used to minimize movement of the tongue of a patient during sedation. An instrument passage 195 may be used to allow medical instruments to pass through the mouthpiece 110.

Figure 18:
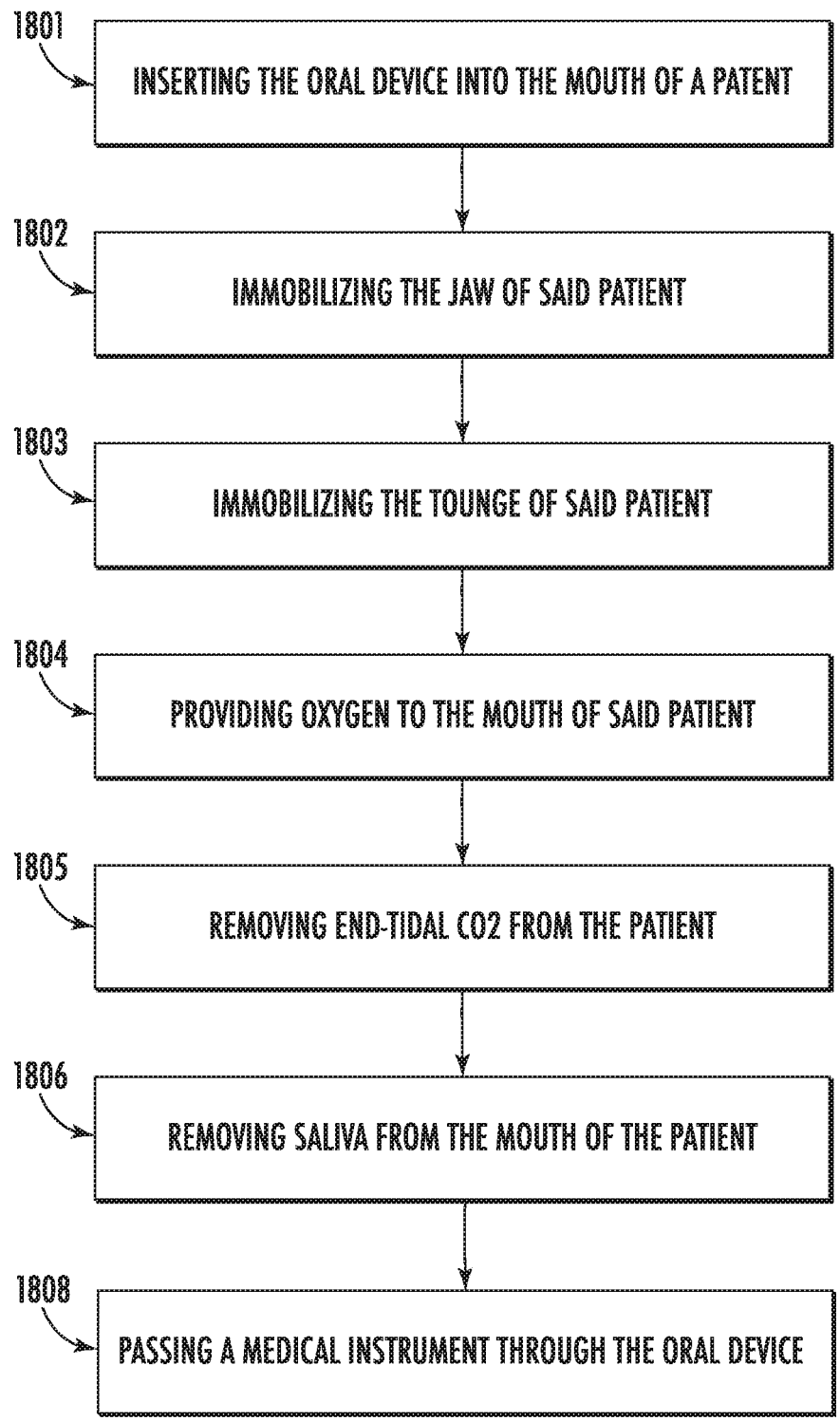
FIG. 18 is a method of using the oral device.

FIG. 18 illustrates a method 1800 to use the oral device 100 during sedation. First at step 1801, a user inserts the oral device 100 into the mouth of a patient. Next, at step 1802, the jaw of a patient is immobilized. The upper portion of the mouthpiece 120 and lower portion of the mouthpiece 130 engage the teeth of a patient and immobilizing the jaw of the patient. At step 1803, the tongue stabilizer 190 engages the tongue of a patient to immobilize the tongue of the patient. At step 1804, a user may provide oxygen to the mouth of the patient. At step 1805, a user may remove end-tidal carbon dioxide from the mouth of the patient. At step 1806, a user may remove secretions from the mouth of a patient, such as saliva. At step 1808, a user may pass a medical instrument through the oral device 100 and into the mouth, for example a camera.

Furthermore, while the particular preferred embodiments of the present invention have been shown and described, it will be obvious to those skilled in the art that changes and modifications may be made without departing from the teaching of the invention. The matter set forth in the foregoing description and accompanying drawings is offered by way of illustration only and not as limitation.

The invention claimed is:

1. An oral device comprising:
    a mouthpiece configured for insertion into a mouth, said mouthpiece having a vestibular portion, an oral cavity portion, an upper portion and a lower portion, wherein said upper portion is configured to hold upper teeth of said mouth and said lower portion is configured to hold lower teeth of said mouth, and wherein the vestibular portion comprises an outer portion of the mouthpiece that faces cheeks and lips when the mouthpiece is inserted into the mouth, and wherein the vestibular portion comprises a top vestibular portion for the upper portion of the mouthpiece and a bottom vestibular portion for the lower portion of the mouthpiece;
    a gas inlet conduit adjacent to and extending directly along a first side of said top vestibular portion of said mouthpiece, wherein said gas inlet conduit has a first opening configured to be outside said mouth and a second opening configured to be inside said mouth and is configured to allow gas to flow from said first opening to said second opening of said gas inlet conduit;
    a gas outlet conduit adjacent to and extending directly along a second side of said top vestibular portion of said mouthpiece, wherein said gas outlet conduit has a first opening configured to be outside said mouth and a second opening configured to be inside said mouth and is configured to allow gas to flow from said second opening to said first opening of said gas outlet conduit; and,
    a saliva outlet conduit directly adjacent to said bottom vestibular portion of said mouthpiece, wherein said saliva outlet conduit has a first opening configured to be outside said mouth and a second opening configured to be inside said mouth and is configured to allow saliva to flow from said second opening to said first opening of said saliva outlet conduit.

2. The oral device of claim 1, wherein said mouthpiece further includes a tongue stabilizer.

3. The oral device of claim 2, wherein said tongue stabilizer has a first element that extends from an anterior of said lower portion of said mouthpiece to a posterior of said mouthpiece and a second element that extends from the anterior of said lower portion of said mouthpiece to the posterior of said mouthpiece.

4. The oral device of claim 3, wherein said first element and said second element of said tongue stabilizer partially overlap.

5. The oral device of claim 1, further comprising a second saliva outlet conduit adjacent to said vestibular portion of said mouthpiece, wherein said second saliva outlet conduit has a first opening configured to be outside said mouth and a second opening configured to be inside said mouth and is configured to allow saliva to flow from said second opening to said first opening of said second saliva outlet conduit.

6. The oral device of claim 5, wherein said second saliva outlet conduit is attached to the lower portion of said mouthpiece.

7. The oral device of claim 1, wherein said saliva outlet conduit further includes a third opening, said third opening configured to be inside said mouth and is configured to allow saliva to flow from said third opening to said first opening of said saliva outlet conduit.

8. The oral device of claim 1, wherein said saliva outlet conduit further includes an opening on a side of said saliva outlet conduit.

9. The oral device of claim 1, wherein said mouthpiece further includes a saliva outlet port located at an anterior portion of the lower portion of the mouthpiece.

10. The oral device of claim 1, wherein said mouthpiece further includes an instrument passage.

11. The oral device of claim 1, wherein said gas inlet conduit and said gas outlet conduit are attached to the upper portion of said mouthpiece.

12. The oral device of claim 1, wherein said saliva outlet conduit is attached to the lower portion of said mouthpiece.

13. The oral device of claim 1, wherein said gas inlet conduit further includes a third opening, said third opening configured to be inside said mouth and is configured to allow gas to flow from said first opening to said third opening of said gas inlet conduit.

14. The oral device of claim 1, wherein said gas outlet conduit further includes a third opening, said third opening configured to be inside said mouth and is configured to allow gas to flow from said third opening to said first opening of said gas outlet conduit.

15. An oral device for a patient comprising:
a mouthpiece configured for insertion into a mouth, said mouthpiece having a vestibular portion, an oral cavity portion, an upper portion and a lower portion, wherein said upper portion is configured to hold upper teeth of said mouth and said lower portion is configured to hold lower teeth of said mouth, wherein the vestibular portion comprises an outer portion of the mouthpiece that faces cheeks and lips when the mouthpiece is inserted into the mouth, and wherein the vestibular portion comprises a top vestibular portion for the upper portion of the mouthpiece and a bottom vestibular portion for the lower portion of the mouthpiece;
a gas inlet conduit attached to and extending directly along a first side of the top vestibular portion of said upper portion of said mouthpiece configured to allow oxygen to pass from outside the mouth of said patient to inside the mouth of said patient;
a gas outlet conduit attached to and extending directly along a second side of the top vestibular portion of said upper portion of said mouthpiece configured to allow end-tidal carbon dioxide to pass from inside the mouth of said patient to outside the mouth of said patient; and,
a saliva outlet conduit directly attached to the bottom vestibular portion of said lower portion of said mouthpiece configured to allow saliva to pass from inside the mouth of said patient to outside the mouth of said patient.

16. The oral device of claim 15, wherein said mouthpiece further comprises at least one outlet port configured to allow saliva to pass from inside the mouth of said patient to outside the mouth of said patient.

17. The oral device of claim 15, further comprising a second saliva outlet conduit attached to said lower portion of said mouthpiece configured to allow saliva to pass from inside the mouth of said patient to outside the mouth of said patient.

18. The oral device of claim 15, wherein said mouthpiece further comprises a tongue stabilizer for immobilizing the tongue.

19. The oral device of claim 15, wherein said mouthpiece further comprises an instrument passage.

\* \* \* \* \*